United States Patent [19]

Secrist, III et al.

[11] Patent Number: 4,985,434
[45] Date of Patent: Jan. 15, 1991

[54] 7-SUBSTITUTED DERIVATIVES OF 2-AMINO-3H,5H-PYRROLO(3,2-D)PYRIMIDIN-4-ONES AND PHARAMCEUTICAL USES AND COMPOSITIONS CONTAINING THE SAME

[75] Inventors: John A. Secrist, III; John A. Montgomery; Steve E. Ealick, all of Birmingham, Ala.; Mark D. Erion, Livingston; Wayne C. Guida, Fanwood, both of N.J.

[73] Assignee: Biocryst, Inc., Birmingham, Ala.

[21] Appl. No.: 429,098

[22] Filed: Oct. 31, 1989

[51] Int. Cl.$^5$ ................. C07D 487/02; A61K 31/495
[52] U.S. Cl. .................................... 514/248; 544/280
[58] Field of Search ........................ 544/280; 514/258

[56] References Cited

U.S. PATENT DOCUMENTS 4,921,858 5/1990 Malone et al. ...................... 544/280
4,923,872 5/1990 Kostlan et al. ...................... 544/280

OTHER PUBLICATIONS

Lim et al., J. Org. Chem., vol. 44, No. 22, 1979, p. 3826.
Lim et al., Tetrahedron Letters, vol. 21, pp. 1013–1016 (1980).
Lim et al., J. Org. Chem., 1983, 48, 780–788.

Primary Examiner—Cecilia Shen
Attorney, Agent, or Firm—Wegner, Cantor, Mueller & Player

[57] ABSTRACT

Disclosed is a compound containing 2-amino-7-(R)-3H,5H-pyrrolo[3,2-d]pyrimidin-4-one wherein R is optionally substituted cyclohexenyl or cyclohexyl, a pharmaceutical composition containing the compound, and a method for the selective suppresion of mammalian T-cell function without diminished effect on humoral immunity which involves administering the composition to a mammal.

14 Claims, No Drawings

7-SUBSTITUTED DERIVATIVES OF 2-AMINO-3H,5H-PYRROLO(3,2-D)PYRIMIDIN-4-ONES AND PHARAMCEUTICAL USES AND COMPOSITIONS CONTAINING THE SAME

The present invention relates to derivatives of 2-amino-3H,5H-pyrrolo [3,2-d]pyrimidin-4-one.

Purine nucleoside phosphorylase (PNP) catalyzes the phosphorolysis of purine nucleosides in a reversible reaction. Individuals who are deficient in PNP exhibit impaired T-cell development, resulting in lowered cell-mediated immunity, but normal B-cell development, resulting in normal humoral immunity. Accordingly, specific inhibitors of PNP that selectively inhibit T-cell development without damaging humoral immunity could be potentially effective against disorders in which activated T-cells are pathogenic.

Accordingly, the present invention is a PNP inhibitor that is a derivative of 2-amino-3H,5H-pyrrolo[3,2-d]pyrimidin-4-one.

In a first aspect of the invention there is provided a compound (I) 2-amino-7-(R)-3H,5H-pyrrolo[3,2-d]pyrimidin-4-one wherein the R group is unsubstituted or substituted 1-, 2-, or 3-cyclohexenyl or cyclohexyl. In a preferred aspect, R is unsubstituted, i.e., the compound (I) is 2-amino-7-(1-cyclohexenyl)-3H,5H-pyrrolo [3,2-d]pyrimidin-4-one (IA), 2-amino-7-(2-cyclohexenyl)-3H, 5H-pyrrolo[3,2-d]pyrimidin-4-one (IB), 2-amino-7-(3-cyclohexenyl)-3H, 5H-pyrrolo[3,2-d]-pyrimidin-4-one (IC), or 2-amino-7-(cyclohexyl)-3H,5H-pyrrolo[3,2-d]-pyrimidin-4-one (ID). In an alternative preferred embodiment the R has at least one substituent selected from the group consisting of halogen, hydroxy, alkoxy, alkyl, or trifluoromethyl. As halogen is preferably mentioned chloro or fluoro. As alkoxy is preferably lower alkoxy, including methoxy, ethoxy, propoxy and butoxy. As alkyl is preferably mentioned lower alkyl, including methyl, ethyl, propyl and butyl.

In a second aspect of the invention there is provided a method for the selective suppression of mammalian T-cell function without diminished effect on humoral immunity which comprises administering to a mammal the compound (I), whereby said compound inhibits purine nucleoside phosphorylase and thereby T-cell formation.

In a further aspect of the present invention there is provided a pharmaceutical composition for the selective suppression of mammalian T-cell function without diminished effect on humoral immunity which comprises an effective amount of the compound (I) and a pharmaceutically acceptable diluent therefor.

The invention further relates to pharmaceutical compositions suitable for enteral, such as oral or rectal, transdermal and parenteral administration to mammals including man, which are useful to inhibit purine nucleoside phosphorylase activity and for the treatment of disorders responsive thereto, comprising an effective amount of a pharmacologically active compound of the invention, alone or in combination, with one or more pharmaceutically acceptable carriers.

Preferred pharmaceutical compositions are tablets and gelatin capsules comprising the active ingredient together with (a) diluents, e.g., lactose, dextrose, sucrose, mannitol, sorbitol, cellulose and/or glycine; (b) lubricants, e.g., silica, talcum, stearic acid, its magnesium or calcium salt and/or polyethyleneglycol; for tablets also (c) binders, e.g., magnesium aluminum silicate, starch paste, gelatin, tragacanth, methylcellulose, sodium carboxymethylcellulose and/or polyvinylpyrrolidone; if desired (d) disintegrants, e.g., starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with a carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

The present invention provides a method of inhibiting purine nucleoside phosphorylase activity in mammals and treating diseases and conditions responsive thereto, e.g., autoimmune disorders, rejection of transplantation or psoriasis, which comprises administering to a mammal in need thereof an effective amount of a compound of the invention or of a pharmaceutical composition comprising a said compound in combination with one or more pharmaceutically acceptable carriers.

A further aspect of the invention relates to a method of inhibiting the phosphorolysis and metabolic breakdown of antiviral or antitumor purine nucleosides in mammals which comprises administering in conjunction therewith to a mammal in need thereof, either separately or in combination therewith, an effective purine nucleoside phosphorylase inhibiting amount of a compound of the invention or of a said compound in combination with one or more pharmaceutically acceptable carriers. More particularly, such relates to a method of inhibiting the phosphorolysis and metabolic breakdown of purine nucleosides known in the art, e.g., of 2'-deoxyguanosine, 2',3'-dideoxyinosine, 2',3'-dideoxyguanosine or 2',3'-dideoxyadenosine.

Furthermore, the invention thus relates to a method of potentiating the antiviral or antitumor effect of 2' or 3'-monodeoxypurine nucleosides or of 2',3'-dideoxypurine nucleosides in mammals which comprises administering in conjunction therewith to a mammal in need thereof, either separately or in combination with a said nucleoside, an effective purine nucleoside phosphorylase inhibiting amount of a compound of the invention preferably in combination with one or more pharmaceutically acceptable carriers. More particularly, such relates to a method of enhancing or potentiating the effect of 2',3'-dideoxypurine nucleosides known in the art, e.g., of 2',3'-dideoxyinosine, 2',3'-dideoxyguanosine or 2'-3'-dideoxyadenosine for the treatment of retrovirus infections, e.g., HIV-retrovirus infections (acquired immunodeficiency syndrome, AIDS). 2',3'-Dideoxypurine nucleosides are known in the art as inhibitors of HIV retrovirus infectivity and to be metabolically degraded by PNP, e.g., as described in *Biochemical Pharmacology* 22, 3797 (1987). Such are administered at a pharmaceutically acceptable dose which is effective in inhibiting HIV-retrovirus infections. Preferably the lowest possible effective dose is used.

The pharmaceutically acceptable effective dosage of active compound of the invention to be administered is dependent on the species of warm-blooded animal (mammal), the body weight, age and individual condition, and on the form of administration.

The pharmaceutical composition may be oral, parenteral, suppository or other form which delivers the compound (I) into the bloodstream of a mammal to be treated. An oral form has from about 1 to about 150 mg of the compound (I) for an adult (50 to 70 kg) which is mixed together with pharmaceutically acceptable diluents such as lactose. In a typical capsule, 25 mg of the compound (I) are mixed together with 192 mg lactose, 80 mg modified starch and 3 mg magnesium stearate. Injectable forms of the compound are also contemplated for administration.

The present invention is also useful with other therapeutic agents. A daily dosage for a human weighing 50 to 70 kg of 1-50 mg/kg inhibits metabolic destruction of certain anticancer agents such as beta-2'-deoxy-6-thioguanosine and antiviral agents such as 2',3'-dideoxyinosine, an anti-AIDS drug. These types of agents are known to be susceptible to cleavage. Upon cleavage, the agents lose effectiveness. The compounds of the present invention are capable of reducing such cleavage. This protection, therefore, enhances the efficacy of other chemotherapeutic agents.

A preferred method of making the compound of the present invention uses a known compound, i.e., cyclohexenylacetonitrile, as the starting material. The compound (I) of the present invention is made by reacting the starting material in an adaptation of the synthetic methodology disclosed in M. I. Lim, R. S. Klein, and J. J.Fox, *J. Org. Chem.*, 44, 3826 (1979); M. I. Lim, R. S Klein, and J. J. Fox, *Tetrahedron Lett.*, 21, 1013 (1980); M. I. Lim and R. S. Klein, *Tetrahedron Lett.*, 22, 25 (1981); M. I. Lim, W. Y. Ren, B. A. Otter, and R. S. Klein, *J. Org. Chem.*, 48, 780 (1983). Catalytic hydrogenation of either (IA), (IB), or (IC) yields the compound (ID).

In order to more fully describe the present invention the following non-limiting examples are provided. In the examples all parts and percentages are by weight unless indicated otherwise. Solvent mixtures used as chromatographic eluents are given in proportions by volume.

EXAMPLE 1

1-Cyclohexenylacetonitrile is treated in the synthesis of the present invention. Under an atmosphere of dry $N_2$, a solution of 1-cyclohexenylacetonitrile (9.2 g; 75.92 mmole) in anhydrous tetrahydrofuran (THF, 10 ml) is added to a stirred mixture of sodium hydride (3.18 g; 132.86 mmole) and ethylformate (30.14 g; 406.93 mmole) in 50 ml THF, and the resulting mixture is stirred at room temperature for about 18 hours. Volatile matter is evaporated in vacuo at room temperature. Water (30 ml) is added to the residue at 0° C., and the solution adjusted to a pH of 6 by dropwise addition of 6N HCl. The resulting precipitate of heavy oil is extracted into $CHCl_3$. The extract is washed with water and dried with $Na_2SO_4$, and the resulting organic layer evaporated to give a crude formyl compound as a red-brown oil (9.6 g).

EXAMPLE 2

Glycine methyl ester hydrochloride (16.68 g, 132.85 mmole) and anhydrous sodium acetate (10.89 g, 132.85 mmole) are added to a solution of the crude formyl compound (9.6 g) of Example 1 without further purification in $MeOH/H_2O$ (4:1, 150 ml). After 24 hours, the MeOH is evaporated in vacuo, and the mixture of water and oil is extracted with $CHCl_3$. The $CHCl_3$ layer is dried ($Na_2SO_4$) and evaporated to give an amber oil which is applied to a silica gel column. Elution with $CHCl_3$ gave the desired enamine: yield 4.5 g.

EXAMPLE 3

Under a nitrogen atmosphere, ethyl chloroformate (3.04 g; 28.06 mmole) is added dropwise to a solution of the enamine of Example 2 (4.12 g, 18.70 mmole) and 1,5-di-azabicyclo[4.3.0]-non-5-ene (DBN, 6.96 g, 56.11 mmole) in dry $CH_2Cl_2$ (100 ml) with external cooling in an ice bath. After stirring at 0° C. for one hour, the solution is allowed to stand at room temperature overnight. After checking progress by TLC, additional $ClCO_2Et$ (0.5 ml) and DBN (3.0 ml) are added to complete the conversion, and the solution is allowed to stand for 24 hours. Volatile matter is evaporated in vacuo, the viscous residue purified on a short silica gel column (whose main purpose is to remove the less-mobile DBN) to give an N-blocked pyrrole, which is used for the next step without further purification.

EXAMPLE 4

To a solution of the N-blocked pyrrole of Example 3 (3.0 g, 10.26 mmole) in MeOH (100 ml) is added solid $Na_2CO_3$ (2.71 g, 25.65 mmole), and the reaction mixture is stirred at room temperature for 48 hr with separation of the resultant deblocked pyrrole. The mixture is evaporated to dryness, and the residue is triturated thoroughly with $H_2O$ (50 ml) to dissolve inorganics and extracted with $CHCl_3$ (3×50 ml). The extract is dried ($Na_2SO_4$) and evaporated to give a viscous gum, which is purified on a silica gel column using $CHCl_3$ as the eluent; yield 2.04 g; m.p. 125° C.

EXAMPLE 5

Benzoyl isothiocyanate (0.76g, 4.65 mmole) is added dropwise to a solution of the unblocked pyrrole of Example 4 (0.91 g, 4.13 mmole) in dry $CH_2Cl_2$ (30 ml). After 1 h at room temperature, the solution is evaporated, and the gummy residue is triturated with methanol to give a thioureido product; yield 0.70 g; m.p. 170° C.

EXAMPLE 6

Methyl iodide (0.678 g, 4.78 mmole) is added to a solution of the thioureido product of Example 5 (0.630 g, 1.64 mmole) and DBN (0.230 g, 1.85 mmole) in dry $CH_2Cl_2$ (50 ml) at 0° C. The solution is stirred at 0° C. for 15 min., at ambient temperature for 1 h, and then evaporated in vacuo. A solution of the residue in $CHCl_3$ is chromatographed on a silica gel column with $CHCl_3$ as eluent to give homogeneous fractions of the methylthio intermediate; yield 0.7 g.

EXAMPLE 7

A solution of the methylthio compound of Example 6 (0.70 g, 1.76 mmole) in 50 ml of MeOH that has been saturated with NH$_3$ at 0° C. is heated at 90°–95° C. for 24 hours in a glass-lined stainless steel bomb. The contents of the chilled bomb are evaporated in vacuo to give a mixture of the compound (IA), benzamide and a by-product that is a 2-methylthio derivative, as opposed to the 2-amino compound (IA). The mixture is stirred vigorously for several minutes with appr. 50 ml of Et$_2$O, and the insoluble white solid is filtered off and washed with Et$_2$O. The filtrate contained most of the benzamide and 2-methylthio components. A solution of the Et$_2$O-insoluble solid (0.342 g) in MeOH is evaporated with appr. 10 g of silica gel. The powdered residue is layered evenly onto the top of a silica gel column, which is then eluted with CHCl$_3$/MeOH/HOAc (95:5:1) to give the 2-methylthio by-product and the desired 2-amino product (IA). (IA) is recrystallized by extraction into boiling isopropyl acetate in a Soxhlet apparatus. The white crystals are collected in three crops and dried in vacuo over P$_2$O$_5$ at 110° C. for 7h; yield 44%; mp 280° C. dec., anal. calcd. for C$_{12}$H$_{14}$N$_4$O.0.6H$_2$O: C, 59.78; H. 6.35; N, 23.23. Found: C, 59.98; H, 6.46; N, 23.15.

EXAMPLE 8

The compound of Example 7 is tested for enzyme-inhibition activity. A purine nucleoside phosphorylase (PNP) enzyme assay is performed in which PNP activity for the compound is determined radiochemically by measuring the formation of [$^{14}$C]-hypoxanthine from [$^{14}$C]-inosine (see *Biomedicine*, 33, 39 (1980) using calf spleen as the enzyme source. At 1 mM phosphate the IC$_{50}$ is 1.9 μM, and at 50 mM phosphate the IC$_{50}$ is 19 μM.

EXAMPLE 9

Following the procedures set forth in Examples 1–7, compounds (IB) and (IC) are made using 2- and 3-cyclohexenylacetonitrile, respectively, as starting materials. The compounds are tested as in Example 8 and significant enzyme-inhibition activity is observed.

EXAMPLES 10–14

The following compounds of the present invention are prepared that are 2-amino-7-(R)-3H,5H-pyrrolo[3,2-d]pyrimidin-4-ones in which the R group is as follows:
Example 10: R=3-methyl-2-cyclohexenyl
Example 11: R=2-chloro-3-cyclohexenyl
Example 12: R=3-trifluoromethyl-1-cyclohexenyl
Example 13: R=3-methoxy-1-cyclohexenyl
Example 14: R=2-fluoro-3-cyclohexenyl The compounds are prepared following the procedures set forth in Examples 1–8 using the appropriate substituted cyclohexenyl acetonitriles as starting materials.

EXAMPLE 15

A pharmaceutical composition for intraperitoneal injection is prepared for testing the compound (IA). An intraperitoneal injection solution containing the compound (IA) is dissolved in an aqueous carrier that contains ten percent DMSO.

EXAMPLE 16

The compound (IA) is intraperitoneally injected into Lewis Rats via the test composition of Example 15 to provide 30 mg of the compound (IA), with an injection given twice per day. Controls are used, which receive only the vehicle. At specific times after administration, the animals are sacrificed and plasma samples are prepared. The plasma is extracted with cold 0.5N HClO$_4$ and neutralized with solid NH$_4$HCO$_3$. After removal of perchlorate salts, the extract is subjected to HPLC on a reversed phase column (Spherisorb ODSI). A significant increase in plasma inosine is observed in the plasma taken from animals receiving the compound (IA).

EXAMPLES 17–21

Compounds prepared as in Examples 10–14 are each made into a pharmaceutical formulation in accordance with the preparation of Example 15 and the resultant injectable solutions are tested in accordance with the procedure of Example 16. A significant increase in plasma inosine is observed in the plasma taken from animals receiving the compounds of the present invention.

EXAMPLE 22

The compound (ID) is prepared using 2-amino-7-(1-cyclohexenyl)-3H, 5H-pyrrolo[3,2-d]pyrimidin-4-one as an intermediate. A solution of the intermediate (0.2 g; 0.86 mmole) in ethanol (50 ml) is hydrogenated with 10% Pd-C (50 mg) at 45 lb/in$^2$ for 16 h and filtered hot through Celite. The filtrate is evaporated to dryness, and the residue is crystallized from hot ethanol to give the compound (ID); yield 157 mg (78%), mp>300° C. dec. anal. calcd. for C$_{12}$H$_{16}$N$_4$O.0. EtOH: C, 61.80; H, 7.10; N, 23.51. Found: C, 61.95; H, 7.43; N, 23.56.

EXAMPLE 23

The compound (ID) prepared in Example 22 is tested for enxyme-inhibition activity as in Example 8. At 1 mM phosphate the IC$_{50}$ is 1.3 μM, and at 50 mM phosphate the IC$_{50}$ is 145 μM.

What is claimed is:

1. A compound of the formula 2-amino-7-(R)-3H5H-pyrrolo[3,2-d]pyrimidin-4-one wherein R is cyclohexyenyl or cyclohexyl optionally substituted by halogen, hydroxy, alkoxy, alkyl or trifluoromethyl.

2. The compound of claim 1 wherein R is 1-cyclohexenyl.

3. The compound of claim 1 wherein R is 2-cyclohexenyl.

4. The compound of claim 1 wherein R is 3-cyclohexenyl.

5. The compound of claim 1 wherein R is cyclohexyl.

6. A method for the selective suppression of mammalian T-cell function without diminished effect on humoral immunity which comprises administering to a mammal the compound of claim 1, whereby said compound inhibits purine nucleoside phosphorylase and thereby T-cell formation.

7. A method for the selective suppression mammalian T-cell function without diminished effect on humoral immunity which comprises administering to a mammal the compound of claim 2, whereby said compound inhibits purine nucleoside phosphorylase and thereby T-cell formation.

8. A method for the selective suppresion of mammalian T-cell function without diminished effect on humoral immunity which comprises administering to a mammal the compound of claim 4, whereby said compound inhibits purine nucleoside phosphorylase and thereby T-cell formation.

9. A method for the selective suppresion of mammalian T-cell function without diminished effect on humoral immunity which comprises administering to a mammal the compound of claim 5, whereby said compound inhibits purine nucleoside phosphorylase and thereby T-cell formation.

10. A pharmaceutical composition for the selective suppresion of mammalian T-cell function without diminished effect on humoral immunity which comprises an effective amount of the compound of claim 1 capable of said selective suppression and a pharmaceutically acceptable carrier or diluent therefor.

11. A pharmaceutical composition for the selective suppresion of mammalian T-cell function without diminished effect on humoral immunity which comprises an effective amount of the compound of claim 2 capable of said selective suppression and a pharmaceutically acceptable carrier or diluent therefor.

12. A pharmaceutical composition for the selective suppresion of mammalian T-cell function without diminished effect on humoral immunity which comprises an effective amount of the compound of claim 3 capable of said selective suppression and a pharmaceutically acceptable carrier or diluent therefor.

13. A pharmaceutical composition for the selective suppresion of mammalian T-cell function without diminished effect on humoral immunity which comprises an effective amount of the compound of claim 4 capable of said selective suppression and a pharmaceutically acceptable carrier or diluent therefor.

14. A pharmaceutical composition for the selective suppresion of mammalian T-cell function without diminished effect on humoral immunity which comprises an effective amount of the compound of claim 5 capable of said selection suppression and a pharmaceutically acceptable carrier or diluent therefor.

* * * * *